United States Patent [19]

Toomey

[11] Patent Number: 5,290,404

[45] Date of Patent: Mar. 1, 1994

[54] ELECTRO-SYNTHESIS OF ALCOHOLS AND CARBOXYLIC ACIDS FROM CORRESPONDING METAL SALTS

[75] Inventor: Joseph E. Toomey, Indianapolis, Ind.

[73] Assignee: Reilly Industries, Inc., Indianapolis, Ind.

[21] Appl. No.: 606,591

[22] Filed: Oct. 31, 1990

[51] Int. Cl.$^5$ ................................................. C25B 3/00
[52] U.S. Cl. .................................... 204/72; 204/59 R; 204/96; 204/98; 204/100
[58] Field of Search ...................... 204/73 R, 72, 59 R, 204/98, 100, 103, 96, 98, 101, 182.4, 77

[56] References Cited

U.S. PATENT DOCUMENTS

| | | | |
|---|---|---|---|
| 2,592,686 | 4/1952 | Groombridge et al. | 204/72 |
| 2,737,486 | 3/1956 | Bodamer | 204/72 |
| 2,770,588 | 11/1956 | Okada et al. | 204/72 |
| 2,967,806 | 1/1961 | Osborne et al. | 204/72 |
| 3,666,647 | 5/1972 | Kubo et al. | 204/182.4 |
| 3,896,011 | 7/1975 | Isoya et al. | 204/59 R |
| 4,101,391 | 7/1978 | Hallcher | 204/59 R |
| 4,589,963 | 5/1986 | Cipriano et al. | 204/72 |
| 4,639,296 | 1/1987 | Cook | 204/59 R |
| 4,808,284 | 2/1989 | Bedell et al. | 204/72 |
| 4,917,781 | 4/1990 | Sharifian et al. | 204/72 |

FOREIGN PATENT DOCUMENTS 2237612  7/1972  Fed. Rep. of Germany .

OTHER PUBLICATIONS

Muller, "Electrochemical Synthesis of 4,4,4-Trifluoro-Butanal", Journal of Organic Chemistry, vol. 49, No. 23 4559-4560 (1984).

Primary Examiner—John Niebling
Assistant Examiner—Kishor Mayekar
Attorney, Agent, or Firm—Woodard, Emhardt, Naughton, Moriarty & McNett

[57] ABSTRACT

A preferred electrochemical process for producing an alcohol or carboxylic acid from a corresponding metal salt while also recovering metal cation residues is described. The preferred process does not require a three-compartment desalination cell but rather can be performed in a standard two-compartment cell divided by a cation-permeable membrane. The process comprises the step of electrolyzing an aqueous medium containing the metal salt in the anolyte of the cell to thereby yield alcohol or carboxylic acid in the anolyte and pass the metal cation into the catholyte. In one particularly preferred mode, the process provides a highly effective recovery of valuable materials from byproduct streams of base-catalyzed syntheses of polyols such as such as trimethylolpropane or pentaerythritol from aldehydes, and in another provides an efficient recovery of phenol.

11 Claims, No Drawings

ELECTRO-SYNTHESIS OF ALCOHOLS AND CARBOXYLIC ACIDS FROM CORRESPONDING METAL SALTS

BACKGROUND

This invention relates to an electro-synthetic method for producing alcohols and carboxylic acids from their corresponding metal salts while also recovering valuable metal cation residues free of the alcohols and carboxylic acids. In so doing, this invention provides desirable synthetic routes to alcohols and carboxylics, as well as highly effective treatments of mediums containing the metal salts, including for instance byproduct streams, to recover valuable products therefrom.

As further background, alcohols, carboxylic acids, and metal cation salts all enjoy wide varieties of uses. Alcohols, for instance, are widely used for organic synthesis, as solvents, detergents, beverages, pharmaceuticals, plasticizers, and fuels, while carboxylic acids find utility in organic synthesis as well as many other applications. Further, metal cation salts include some of the most widely used chemicals in the world. For instance, metal hydroxides, e.g. sodium hydroxide and magnesium hydroxide, are used in very large quantities in chemical manufacture, refining, and in the production of pulp and paper, detergents, textile processing, etc.

The alkalai metal salt counterparts of carboxylic acids and alcohols are also useful in organic syntheses and other applications. However, there are many situations in which it would be most desirable to convert these alkalai metal salts to their corresponding alcohols or carboxylic acids. Further, because metal cation salts such as caustic materials (e.g. alkali metal hydroxides) are considered valuable and relatively expensive especially by those familiar with their high-volume use in many commercial scale reactions and other settings, it would also be highly desirable to be able to recover the metal cation residues liberated during such conversions, for instance as hydroxide salts.

As an example, large quantities of alkalai metal (e.g. sodium) salts of carboxylic acids are present in the byproduct stream from production of trimethylolpropane (TMP), a large-volume intermediate primarily used as a glyceride substitute in alkyd resins, in flexible urethane foams, and in synthetic lubricant base stocks. See, *Chemical Economics Handbook*, SRI International, pages 682.7001 U and W, 682.7002 V, and 682.7003 I (August 1985). TMP is currently made by reaction of three equivalents of formaldehyde with n-butyraldehyde. The initial step is a condensation reaction catalyzed by base (e.g. NaOH) and thus little if any NaOH is used in this step. However, the final step of the reaction is not catalytic: it is a Cannizzaro reaction in which an entire equivalent of caustic base is consumed, producing TMP and sodium formate. The byproduct stream from this TMP synthesis has an equivalent of sodium formate. In this instance, significant commercial and technical advantage could be gained from conversion of the sodium formate to formic acid, while also recovering the valuable sodium hydroxide for use in another TMP synthesis or otherwise. An additional benefit would be gained if the treatment of the byproduct stream also allowed for survival and facilitated recovery of any remaining TMP in the byproduct stream.

As another example, phenol is a valuable alcohol having many and diverse uses. Currently, most phenol worldwide is made by oxidation of cumene, with acetone occurring as a byproduct. The initial reaction step yields cumene hydroperoxide, which decomposes with dilute sulfuric acid to form the phenol and acetone as primary products. As a result, the commercial supply of acetone is largely tied to its occurrence as a byproduct in the production of phenol.

Minor amounts of phenol are produced by still other routes. For example, some is produced by the Dow process in which chlorobenzene is reacted with sodium hydroxide at elevated temperatures to form sodium phenoxide and sodium chloride. The phenoxide is then treated with hydrochloric acid to yield phenol. Another less-used route to phenol involves the fusion of benzenesulfonate with alkali at elevated temperatures to form sodium phenoxide, which is then treated with dilute $H_2SO_4$ to yield the phenol. These processes are undesirable because two equivalents of valuable sodium hydroxide are consumed.

It is evident from the foregoing that the need exists for improved synthetic routes to alcohols and carboxylics. Equally evident is the need for an improved way to treat mediums containing corresponding metal salts of alcohols or carboxylic acids, including for instance byproduct streams containing metal salts of carboxylic acids, to recover valuable products therefrom in a form that requires little or no further processing prior to use. The applicant's invention addresses these needs.

SUMMARY OF THE INVENTION

In brief summary, one preferred embodiment of the invention relates to an electrochemical process for producing an alcohol or carboxylic acid from a corresponding metal salt while also recovering metal cation residues. The preferred process is performed in a two-compartment cell (as opposed to a standard three-compartment desalination cell) having an anolyte and catholyte separated by a cation-exchange (also commonly referred to as "cation-permeable") membrane, and comprises the step of electrolyzing an aqueous medium containing the salt in the anolyte to therein yield the alcohol or carboxylic acid and pass the metal cation into the catholyte. The invention thus provides important advantages over known desalinations and synthetic routes to alcohols and carboxylic acids. These include, for instance, highly effective recovery of valuable metal cation residues which are also separated from the alcohol or carboxylic acid product thus greatly facilitating its recovery as well. Further, in one particularly preferred embodiment the invention provides a highly advantageous treatment of byproduct streams containing alkalai metal salts, such as byproduct streams from the production of polyols such as trimethylolpropane or pentaerythritol which contain alkalai metal salts of carboxylic acids. As an added embellishment, the applicant has discovered that any residual TMP in such byproduct streams also survives during particularly preferred processes of the invention, and accordingly can also be recovered in addition to the carboxylic acid and metal cation residues.

As will be appreciated, by its provisions this invention provides the above advantages, as well as additional objects and advantages which will be apparent from the following description.

DESCRIPTION OF THE PREFERRED EMBODIMENTS

For the purposes of promoting an understanding of the principles of the invention, reference will now be made to certain preferred embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

In accordance with the discussion above, one preferred embodiment of the invention relates to an electrochemical process by which an alcohol or carboxylic acid is produced from a corresponding metal salt thereof. Such metal salts can accordingly include, for example, carboxylic acid salts such as metal formates, acetates, propionates, butyrates, valerates, benzoates, phthalates, and alkoxide salts such as metal methoxides, ethoxides, propoxides, butoxides, etc. and aryloxide salts such as metal phenoxides, naphthoxides, etc. Representative metal salts will therefore include those of the general formula R—O—M or R—COO—M where M is an alkalai metal, alkaline earth metal, transition metal, valve metal, or noble metal, and R is an alkyl, aryl, or aralkyl group, with preferred groups having from about 1 to about 25 carbon atoms. Preferred metals are alkalai metals (e.g. lithium, sodium, or potassium).

The preferred process is carried out in a two-compartment electrochemical cell divided by a cation-exchange membrane. This two-compartment cell is contrasted to three compartment cells used in standard desalinations. These three-compartment desalination cells have a central compartment into which the medium to be desalinated is placed. The central compartment is divided from an anode compartment by an anion-exchange membrane and from a cathode compartment by a cation-exchange membrane. In contrast, the cell according to the invention has an anode compartment divided from a cathode compartment by a cation-exchange membrane, and the aqueous medium containing the metal salt is placed into the anolyte in d in direct contact with the anode. The inventive process is thus significantly simplified compared to standard desalinations, since any suitable two-compartment cell design can be used, including for instance cells operable in batch or continuous modes, static or flow designs, mixed or unmixed, etc.

In the preferred process, an aqueous medium, preferably a solution, containing the alkalai metal salt is charged into the anode compartment. An aqueous catholyte is also charged into the cell, and the anolyte and catholyte are electrolyzed by the application of current through the cell. Thereby, alcohol or carboxylic acid is yielded in the anolyte as protons formed at the anode protonate the organic anion (e.g. R—O⁻ or R—COO⁻) of the metal salt, while the metal cation is selectively passed into the catholyte which becomes concentrated with metal cation. By the inventive process, an extraordinarily high and cost-efficient yield of alcohol or carboxylic acid and recovery of metal cation residues can thus be achieved. Additionally, the metal cation in the catholyte can be recovered, for instance, in the form of metal hydroxide formed from the metal cation exchange and the production of hydroxyl ions at the cathode. The metal cation can also be recovered in the form of other residues, such as $NaHCO_3$ or $Na_2CO_3$ if a $CO_2$-containing aqueous catholyte is used, or in the form of metal acetate or metal halide if, respectively, dilute aqueous acetic acid or hydrochloric acid catholytes are used.

The process temperatures, amount of current, current densities, EMF's, charge passed and other similar parameters will depend upon the particular chemistries involved. Additionally, the types of anodes and cathodes used will vary according to the chemistries involved. Benefiting from the description herein, those practiced in this area will be able to choose acceptable of these and other similar parameters as necessary to achieve the invention. As to preferred parameters, the inventive process is preferably conducted at temperatures of about 0°–100° C. Further, current densities of about 5 to about 500 $mA/cm^2$ are typical, and charge is preferably passed for at least about 100% of theoretical using EMF's of about 3 to about 20 V.

Turning now to two particularly preferred modes of carrying out the invention, one involves the treatment of the byproduct stream from the synthesis of trimethylolpropane (also known as 2-ethyl-2-hydroxymethylpropane-1,3-diol) and the another involves production of Phenol. As discussed earlier, the TMP synthesis of interest is carried out in very high volume worldwide and involves a sodium-hydroxide-catalyzed condensation of formaldehyde and n-butyraldehyde. The TMP synthesis yields a substantial byproduct stream containing significant unrecovered TMP and sodium formate. Because these potentially valuable materials are present, there has been considerable interest and effort devoted to developing cost-justified treatments of these byproduct streams to yield valuable products. This preferred mode of the invention squarely addresses this need by providing an efficient electrochemical treatment yielding valuable carboxylic acid (e.g. formic acid) and a metal hydroxide (e.g. sodium hydroxide) in separate mediums from which they can be readily recovered.

This preferred mode can be carried out, for example, by charging the aqueous byproduct stream as or into the anolyte of a two-compartment cell divided by a cation-exchange membrane. An aqueous catholyte, preferably a dilute metal hydroxide solution, is also charged. As current is applied: cations are selectively passed into the catholyte, where, in combination with $OH^-$ produced at the cathode ($H_2O + 1e^- \rightarrow OH^- + \frac{1}{2} H_2$), a metal hydroxide-enriched solution is formed; and protons formed at the anode ($H_2O \rightarrow 2 H^+ + \frac{1}{2} O_2 + 2e^-$) neutralize the carboxylate anion to form a carboxylic acid (e.g. formic acid). An extraordinarily convenient and cost effective recovery of valuable products from the TMP byproduct stream is thereby provided. In this regard, condensations similar to that for TMP are performed on notable scales using aldehydes having varying numbers of carbons to produce varying polyols for purposes similar to TMP. Production of pentaerythritol is one such example. The resulting byproduct streams from these similar syntheses accordingly also contain unrecovered alcohol, as well as other metal salts, such as, for instance, sodium acetate, propionate, etc. This preferred mode is also effectively applied to these other similar byproduct streams, the treatment of which is therefore also within the contemplation and scope of this invention.

As an added advantage, the applicant has discovered that the above processes can be performed with the unrecovered alcohol (e.g. TMP) present in the by-product stream, and further that the alcohol survives when proper anode materials are chosen. In this regard, preferred anode materials at which TMP survives contain nickel or platinum, including for instance nickel, platinum or platinum-coated anodes (e.g. platinum-coated titanium), titanium suboxides (EBONEX ™) or graphite. Otherwise, if the alcohol is not present or is not to be recovered, the above-mentioned or any of a large number of other anode materials can be used, including for instance iron oxides, copper oxides and others. As to cathode materials, any suitable material at which hydroxyl ions are formed from an aqueous medium under the reaction conditions is acceptable, including for example titanium, lead, graphite, copper, nickel, zinc, steel, silver, and others. From work to date, the applicant has preferred titanium. Typically, current densities used will range from about 5 to about 500 mA/cm$^2$, with more preferred current densities being about 15 to about 150 mA/cm$^2$. Additionally, although readily be determined by those practiced in this field, preferred temperatures are about 25°–80° C.

In the preferred mode for producing phenol, a metal phenolate salt, preferably an alkalai salt such as sodium phenolate, is charged into the anolyte of a two-compartment cell divided by a cation exchange membrane. This phenolate can be of any source, including for instance phenolate formed by reaction of sodium hydroxide with a suitable substituted benzene as known therefor in the art (e.g. chlorobenzene or benzenesulfonate), or phenolate present in a byproduct stream from whatever source. The cell is also provided with an aqueous catholyte. Current is applied to the cell during which the phenolate is protonated to form phenol (protons formed at the anode), and during which sodium cations are selectively passed into the catholyte, where, in combination with hydroxyl ions formed at the cathode, they form a sodium hydroxide-enriched medium. A suitable anode is used for this reaction which does not cause any significant oxidation of the phenolate such as to quinone. Such suitable anodes include for instance platinum-containing anodes, e.g. platinum or platinum-coated anodes, and anodes of or containing gold, rhodium, silver, or nickel. As in the preferred mode discussed above, many suitable cathode materials can be used, for instance titanium, lead, graphite, copper, nickel, zinc, steel, silver, and others, although titanium has been preferred to date. Likewise, while not necessary, the reaction is preferably performed at about 25 to about 80° C. Similarly, i preferred current densities are about 5 to 500 mA/cm$^2$, and more preferably about 15 to 150 mA/cm$^2$. This preferred mode can thus provide an efficient production of phenol with concurrent recovery of caustic residues from the alkalai phenolate reactants.

While the invention has been described in detail in the foregoing description, the same is to be considered as illustrative and not restrictive in character, it being understood that only the preferred embodiments have been described and that all changes and modifications that come within the spirit of the invention are desired to be protected. To facilitate a further understanding of the principles and advantages of the invention, the following illustrative Examples are provided.

EXAMPLE 1

A solution containing 2.4 g (35 mmol) sodium formate, 4.0 g (30 mmol) 2-ethyl-2-hydroxymethylpropane-1,3-diol (trimethylolpropane) and 0.20 g (1.7 mmol) of sodium dihydrogenphosphate in 22.3 g water was circulated by a GILSON peristaltic pump, equipped with a high flow pump head, at 40 mL/min through the anode compartment of a flow cell. The electrochemical cell had planar electrodes with a 10 cm$^2$ surface area (each), a 9 mm electrode gap, and no turbulence promoters. Glass reservoirs were used for the compartments, without external cooling. The cell had a platinum-coated (100 microinch thickness) titanium anode and a titanium cathode, and a NAFION cation-permeable membrane separated the anode and cathode compartments. The catholyte was 60 g of 5% aqueous sodium hydroxide solution. The anolyte and catholyte were electrolyzed at 27°–31° C. by passing 0.50 A (current density=50 mA/cm$^2$) through the cell at applied EMF's of 4.8 to 7.3 V until a total of 3405 Coulombs (100% of theoretical charge) had been passed. NMR analysis of the resulting colorless anolyte by the recognized known-addition method showed quantitative recovery of both the triol and formic acid. The resulting catholyte was enriched in sodium hydroxide. Titration of the caustic indicated excellent recovery of sodium residues as NaOH (greater than 99%). Analogous results obtain where sodium formate is replaced by sodium acetate, propionate, butyrate, valerate, benzoate or phthalate, and where each of these sodium salts is replaced by a corresponding potassium, iron, or calcium salt. Additionally, similar results obtain with each of these salts were a platinum anode or graphite anode is used instead of the platinum-coated titanium anode.

EXAMPLE 2

A solution of 7.5 g (0.11 mole) sodium formate and 0.15 g (1.3 mmol) sodium dihydrogenphosphate in 22.3 g of water was circulated through the anode compartment of a cell as described in Example 1 above. The cell had a nickel anode, a titanium cathode, and a NAFION cation-permeable membrane. The catholyte was 60 of 5 wt.% aqueous sodium hydroxide solution. The anolyte and catholyte were electrolyzed at 26° to 27° C. by passing 0.50 A (current density=50 mA/cm$^2$) through the cell at applied EMF's of 4.0 to 5.1 V until 1.06E4 Coulombs (100% of theoretical charge) had been passed. NMR analysis of the resulting light yellow anolyte by the known addition method showed quantitative recovery of formic acid. A slight amount of a precipitate, possibly nickel formate, appeared in the processed anolyte after overnight storage. This procedure was repeated except this time the anolyte also contained 4.0 g (30 mmol) trimethylolpropane. The results were again sucessful, showing quantitative recovery of sodium formate and the triol in a slightly yellow anolyte also containing only a small amount of precipitate. Similar successful results also occur where sodium formate is replaced by sodium acetate, propionate, butyrate, valerate, benzoate or phthalate, and where each of these sodium salts is replaced by a corresponding potassium, iron or calcium salt. Use of a copper anode instead of a nickel anode in a similar process produced a large quantity of a blue precipitate, possibly copper formate, and an accompanying high cell resistance under these conditions. In another experiment, the catholyte was an aqueous $KHCO_3$ solution and the anolyte included an aqueous medium containing potassium formate. $CO_2$ was bubbled through the catholyte, whereby potassium bicarbonate was recovered instead of potassium hydroxide.

EXAMPLE 3

A solution containing 8.1 g (86 mmol) phenol and 3.6 g (90mmol) NaOH in 18.3 g of water was circulated through a cell as described in Example 1 above. The cell had a platinum anode, a titanium cathode, and a NAFION cation-permeable membrane. The catholyte was 60 g of 5 wt. % aqueous sodium hydroxide solution. The anolyte and catholyte were electrolyzed at 25°–27° C. by passing 0.40 A (current density=40 $mA/cm^2$) through the cell at applied EMF's of 4.2 to 4.4 V until 1.01E4 Coulombs (120% of theoretical charge) had been passed. NMR analysis of the resulting organic layer of the anolyte showed an 80% yield of recovered phenol. The aqueous layer of the anolyte had an additional 8% phenol. Total recovery was thus 88%. The resulting catholyte was enriched in sodium hydroxide. Similar successful results were achieved where a platinum-iridium(IV)oxide anode was used instead of the platinum anode. Analogous results also obtain where sodium phenolate is replaced by sodium methoxide, ethoxide, propoxide, butoxide, or naphthoxide, and where each of these salts is replaced by a corresponding potassium, iron, or calcium salt. In analogous experiments, using aqueous acetic acid as the catholyte resulted in the synthesis of metal acetates in the catholyte.

What is claimed is:

1. A process for producing an alcohol from a corresponding metal salt while also recovering metal cation residues, the process being performed in a two-compartment cell having an anolyte and catholyte separated by a cation-exchange membrane and comprising the steps of: (a) electrolyzing an aqueous medium containing said salt in the anolyte to therein yield said alcohol and pass said metal cation into the catholyte, wherein said electrolyzing is at a current density of between about 15mA/$cm^2$ and about 75 mA/$cm^2$; and (b) recovering said alcohol in a yield of at least about 80% based on the amount of the corresponding metal salt starting material.

2. A process according to claim 1, and also comprising the step of isolating and recovering said alcohol.

3. A process according to claim 2, and also comprising the step of isolating and recovering said metal cation in the form of a metal hydroxide.

4. A process according to claim 3, wherein said cell has a platinum, gold, rhodium, silver, or nickel anode.

5. A process according to claim 4, wherein said metal salt is a metal methoxide, ethoxide, propoxide, butoxide, phenoxide, or naphthoxide.

6. A process according to claim 5, wherein said metal salt is an alkali, alkaline earth, or transition metal salt.

7. A process according to claim 6, wherein said metal salt is an alkali metal salt.

8. A process according to claim 7, wherein said metal salt is a sodium salt.

9. A process according to claim 8, wherein said sodium salt is sodium phenoxide.

10. A process according to claim 9, wherein said cell has a platinum anode.

11. An electrochemical process for producing phenol from a corresponding metal salt while also recovering metal cation residues, the process being performed in a two-compartment cell having an anolyte and catholyte separated by a cation-exchange membrane and comprising the step of electrolyzing an aqueous medium containing said salt in the anolyte to therein yield phenol and pass said metal cation into the catholyte.

* * * * *